United States Patent [19]

Fareed et al.

[11] Patent Number: 4,748,112
[45] Date of Patent: May 31, 1988

[54] METHODS AND COMPOSITIONS RELATING TO REGRESSION-ASSOCIATED ANTIGENS

[75] Inventors: George C. Fareed; Arup Sen, both of Los Angeles, Calif.

[73] Assignee: International Genetic Engineering, Inc., Santa Monica, Calif.

[21] Appl. No.: 837,494

[22] Filed: Mar. 7, 1986

[51] Int. Cl.$^4$ .................... C07K 3/00; C07K 15/00; G01N 33/53; G01N 33/574

[52] U.S. Cl. ............................ 435/7; 424/85; 424/88; 435/29; 436/536; 436/543; 436/548; 436/813; 530/350; 530/387; 530/403; 530/412; 530/413

[58] Field of Search ............ 424/85, 88; 435/7, 29; 436/536, 548, 813, 543; 530/380, 387, 412, 413, 417

[56] References Cited

U.S. PATENT DOCUMENTS

| | | | |
|---|---|---|---|
| 4,340,535 | 7/1982 | Voisin | 424/85 X |
| 4,383,985 | 5/1983 | Bartorelli | 436/813 X |
| 4,452,904 | 6/1984 | Haagensen, Jr. | 436/813 X |
| 4,472,509 | 9/1984 | Gansow | 436/813 X |
| 4,517,303 | 5/1985 | Freytag | 436/813 X |
| 4,543,211 | 9/1985 | Kato | 424/85 X |
| 4,559,311 | 12/1985 | Stenman | 436/813 X |
| 4,562,160 | 12/1985 | Real | 436/813 X |
| 4,584,268 | 4/1986 | Ceriani | 436/813 X |

OTHER PUBLICATIONS

Ben-Aissa et al., *Br. J. Cancer*, 52, 65–72 (1985).
Bubbers et al., *Bull. Cancer*, 68, 332–337 (1981).
Capony et al., *Biochem. Biophys. Res. Commun.*, 108, 8–15 (1982).
Du Bois et al., *J. Immunol. Methods*, 63, 7–24 (1983).
Feit et al., *Cancer Res.*, 44, 5752–5756 (1984).
Giard et al., *J. Nat. Cancer Inst.*, 51, 1417–1423 (1973).
Herrmann et al. *J. Cell Sci*, 73, 87–103 (1985).
Hood et al. *Immunology*, Benjamin/Cummings Publishing Co., 510–529, (1984).
Juillard et al. *Cancer*, 41, 2215–2225 (1978).
Juillard et al. *Bull. Cancer*, 66, 217–228 (1979).
Kohler et al. *Nature*, 256, 495–496 (1975).
Lachmann et al.
*Br. J. Cancer*, 51, 415–417 (1985).
Laemmli *Nature*, 227, 680–685 (1970).
Laucius et al. *Cancer*, 40, 2091–2093 (1977).
Lowder et al. *Western J. Med.*, 143, 810–818 (1985).
Mule et al. *J. Immunol.* 135, 646–652 (1985).
Sell *Monoclonal Antibodies and Cancer Therapy*, A. R. Liss, Inc., New York, 3–21 (1985).
Rodwell et al. *Biotechnology*, 3, 889–894 (1985).
Rosenberg et al. *New Engl. J. Med.*, 313, 1485–1492 (1985).
Sen et al. *Proc. Natl. Acad. Sci.* (USA), 80, 1246–1250 (1983).
Schlom et al. *Cancer*, 54, 2777–2794 (1984).
Springer *Science*, 224, 1198–1206 (1984).
Towbin et al. *Proc. Natl. Acad. Sci.*, (USA), 76, 4350–4354 (1979).
Wallack et al. *Surgery*, 96, 791–800 (1984).
Weisenburger et al. *J. Biol. Resp. Mod.*, 1, 57–66 (1982).

*Primary Examiner*—Sidney Marantz
*Attorney, Agent, or Firm*—Marshall, O'Toole, Gerstein, Murray & Bicknell

[57] ABSTRACT

Regression associated antigens are identified in material from neoplastic cells by their immunological reactivity with regression associated antibodies from the serum of patients diagnosed as undergoing regression of a tumor. Regression associated antibodies are identified by their absence during progression of a neoplastic disease state and by their presence in a diagnosed state of regression. The antigens are purified, used to monitor the condition of cancer patients, and production of antibodies and treatments employing those antibodies are described.

11 Claims, No Drawings

METHODS AND COMPOSITIONS RELATING TO REGRESSION-ASSOCIATED ANTIGENS

BACKGROUND

The present invention pertains in general to antigens associated with tumors and uses therefor, and in particular to regression-associated antigens (RAAs) and uses therefor.

During the past decade much effort has focused on the development of polyclonal and monoclonal antibodies for diagnosis and treatment of cancers. In almost all cases the immunogens have been intact tumor cells or membrane proteins obtained from the cells in order to obtain antibodies directed against tumor cell components. Early work in this field allowed the identification of interesting but not therapeutically useful onco-fetal antigens and blood group antigens [Springer, *Science*, 224, 1198 (1984)]expressed on malignant cells and shed into the bloodstream in some instances. More recently, antigens associated with tumor cells have been identified by immunoblotting methods. Du Bois et al., *J. Immunol. Methods*, 63, 7 (1983). Monoclonal antibodies reactive with the surface of human breast carcinoma cells have been generated and characterized. Schlom et al., *Cancer*, 54 (11 suppl.), 2777–2794 (1984). The immunogens used were membrane-enriched fractions of metastatic carcinoma lesions. One monoclonal antibody reacted with a 220,000 to 400,000 dalton high-molecular weight glycoprotein complex found in 50% of human mammary carcinomas and 80% of human colon carcinomas. A number of equally intriguing monoclonal antibodies reactive with tumor-associated antigens on the surfaces of other human cancers including ovarian, pancreatic and intestinal malignancies have thus been obtained. See the *Proceedings of the UCLA Symposium on Monoclonal Antibodies and Cancer Therapy*, Reisfeld et al., eds., A. R. Liss, Inc., New York (1985).

The antibodies, monoclonal and polyclonal, described to date have been directed against determinants of human tumor cell antigens which may elicit an immune response in test animals chosen for the production of tumor-specific antibodies. It is not known whether patients harboring tumors or treated with specific and/or nonspecific immune stimulants produce antibodies against these antigenic determinants. Therefore, the relevance of such antibodies in mediating regression of tumors in patients is unclear. Passive transfer of such antibodies generated in other animals into patients has met with only a limited success. Lowder et al., *Western J. Med.* 143, 810, (1985).

An interesting clinical approach toward active immunotherapy of tumors involves the generalized stimulation of the patient's own immune system using nonspecific stimulants such as components of the walls of two bacterial cells, *Mycobacterium bovis* (BCG strain) and *Corynebacterium parvum (C. parvum)*, or "detoxified" bacterial endotoxin. In parallel, biological response modifiers such as interleukin 2 have been used to induce activation of the immune system and cause tumor cell destruction. Mule et al., *J. Immunol.*, 135, 646 (1985); and Rosenberg et al., *New Engl. J. Med.*, 313, 1485 (1985).

Concurrently with these efforts attempts have been made to immunize cancer patients with allogenic tumor cell preparations (tumor cell lines obtained from a similar histopathologic tumor from a different patient) as vaccines. This would be expected to specifically stimulate the patient's own immune system to possible unique antigenic structures present on the particular malignant cell type and thus induce tumor regression. Lachman et al. *Br. J. Cancer*, 51, 415–417 (1985); Wallack et al., *Surgery*, 96, 791-800 (1984). Active specific immunotherapy has also been attempted by systematically injecting autochthonous (cells derived from the tumor mass of the same patient) tumor cell vaccines intradermally or subcutaneously. Laucius et al., *Cancer*, 40, 2091 (1977).

SUMMARY OF THE INVENTION

A method for detecting regression-associated antibodies (RAAbs) according to the present invention involves obtaining a first sample of serum from a patient diagnosed as not being in a state of regression and obtaining a second sample of serum from the patient after diagnosis as being in a state of regression. A component of a neoplastic cell is exposed to each of the samples. The presence of an immune complex between an antibody in the second serum sample and the component and the absence of such a complex between the component and an antibody in the first serum sample is indicative of the presence of RAAbs in the second sample. A method for purifying RAAs according to the present invention further involves disrupting the neoplastic cell associated with RAAs as determined by complex formation with an RAAb into components ot a solution, chomatographically separating the component of the solution into fractions and identifying fractions containing RAAs by the presence of immune complex formation of components of a fraction with antibodies to RAAs. A purified and isolated RAA according to the present invention has a molecular weight as determined by reducing SDS polyacrylamide gel electrophoresis to be with the range from about 19000 to about 23000 daltons, or within the range from about 41000 to about 45000 daltons or within the range from about 65000 to about 71000 daltons.

Immunotherapy may be performed according to the present invention by introducing an RAA according to the present invention, a neoplastic cell associated with an RAA according to the present invention, or a membrane fraction of such a neoplastic cell into the lymphatic or hematic fluid (i.e., the lymph or blood) of a patient.

The response of a patient to immunotherapy may be monitored for symptoms associated with a neoplasm by determining a circulating level of RAAbs in a patient. Metastasis may be monitored by determining the level of an RAA in a bodily fluid.

The present invention also provides monoclonal or monospecific polyclonal antibodies exhibiting a specific immunoreactivity with an RAA. An antibody according to the present invention may be purified by contacting a substrate bound RAA with a solution containing an RAAb and eluting the RAAb from the RAA. A monoclonal or monospecific polyclonal antibody according to the present invention may be bound to an anticancer drug and introduced into a bodily fluid of a patient so that the drug is selectively delivered to tumor cells by specificity of the drug-bound antibody to the tumor cell.

DETAILED DESCRIPTION

The present invention concerns properties of antibodies from patients undergoing a cancer immunotherapy protocol and responding with tumor regression. These RAAbs from patient sera have been used to detect tumor-specific designated herein as RAAs in a number of fresh human tumor extracts and in cultured human tumor cell lines.

Previously, discrete antigens associated with cultured human tumor cells have been identified by screening large numbers of monoclonal antibodies produced in mice and other animals against tumor cells or partially fractionated immunogens derived from cancer cells. That approach suffers from two deficiencies: (1) most antibodies directed against such antigens were not associated with the progression or regression of tumors and as such the antigens detected by these antibodies are unlikely to have therapeutic potential as vaccines, and (2) human antigenic determinant(s) which elicit an antibody response in mice might not trigger the human immune surveillance mechanisms against a tumor.

In the present invention, antibodies in sera from patients actively immunized by intralymphatic infusion of their own (autochthonous) tumor cells or tumor cell lines from other patients (allogenic) and characterized by significant tumor regression have been used as the source for specific antibodies associated with tumor regression. These antibodies have been screened using normal and tumor cells as well as tissue extracts to identify specific antigens in tumor cells and tissues. These tumor-associated antigens designated herein as regression-associated antigens can be further grouped based on their sizes, their ability to react with regression-associated antibodies (RAAbs) from patients regressing different malignancies, and their presence on different human cancer cell types.

RAAbs according to the present invention are antibodies which are induced in response to intralymphatic administration of irradiated tumor cell vaccines and are associated with the stabilization or regression of tumor masses.

RAAs according to the present invention include antigens present on human tumor cells which presumably induce the production of RAAbs and which thus may be recognized by antibodies in the sera of patients showing tumor regression in response to tumor cell vaccine administered through the intralymphatic route.

EXAMPLE 1

Detection of specific RAAbs in patients regressing tumor in response to intralymaphatic immunotherapy with tumor cell vaccines: Serum samples are obtained from patients with documented malignancies that are in the state of tumor progression from the primary site of origin to other locations in the body (metastasis).

The patients are then subjected to intralymphatic immunotherapy as described in Juillard et al., *Bul. Cancer*, 66, 217 (1979) which is incorporated by reference herein using infusions of their irradiated tumor cells or irradiated tumor cell lines from other patients with malignancies of the same type as the patient in question as described in Juillard et al., *Cancer*, 41, 2215 (1978); and in Weisenburger et al., *J. Biol. Resp. Mod.*, 1, 57 (1982) both of which are also incorporated by reference herein. The amount of neoplastic cell material used for immunization of patients has been determined and described by Juillard and his colleagues and is presented in published reports including Juillard et al., *Cancer*, 41, 2215-2225, (1978) and is also described in the article of Bubbers et al., *Bull. Cancer*, 68, 332-337 (1981).

Neoplastic cells used in tumor cell line vaccines are defined as cells derived from tumors isolated from cancer patients which cells have an altered karyotype with chromosomal abnormalities and which cells, when allowed to proliferate in culture, have altered growth properties. These altered growth properties include: (a) the loss of anchorage dependent growth and the ability to form masses in semi-solid media; (b) the ability to produce solid tumors in athymic mice; and (c) alterations in membrane structures including the presence of tumor-associated antigens examples of which have been described in the literature, and which are distinct from the antigens described in this invention. See Hood et al., *Immunology*, Benjamin/Cummings Publishing Co., 510-529, (1984); and *Monoclonal Antibodies and Cancer Therapy*, Reisfeld et al., eds., A. R. Liss, Inc., New York, 3-23 (1985).

A state of tumor regression in patients undergoing such intralymphatic immunotherapy is established by evaluating the status of the tumor using several criteria. The evaluation process comprises accepted clinical monitoring procedures including standard radiological evaluations, computerized axial tomography, nuclear magnetic resonance scanning, assessment of various immunological markers for cancers (e.g., carcinoembryonic antigen, newly discovered antigens detected by tumor-specific monoclonal antibodies), tumor-specific enzymes and hormone receptors and other standard laboratory tests used in the clinical management of cancer patients. In addition, a careful physical examination including palpation of tumor nodules is conducted.

Partial tumor regression is indicated if the following is observed. Stabilization of a tumor which was progressing prior to immunotherapy (failure to detect any objective change in tumor size for three months) or less than fifty percent objective response, associated with subjective improvement or status quo. Such stabilization of tumor growth is associated with the development of delayed hypersensitivity to vaccine materials as assessed by subcutaneous and intradermal skin testing of antigens in the cellular vaccines. A successful tumor regression response is defined as an objectively measurable decrease in the size of the tumor mass by at least fifty percent. This is assessed by direct measurement when the tumor is near the surface of the body and directly palpable, by radiological measurements and by the additional criteria cited above.

Serum samples are obtained from these patients at different times after initiation of the immunotherapy. The status of the tumor is assessed as described above. The serum samples from patients undergoing the immunotherapy regimen and responding with tumor regression are tested along with the serum samples from each patient obtained prior to the initiation of immunotherapy and/or before the patient is in a state of regression.

The detection of discrete RAAs is achieved using the Western immunoblotting technique where antibodies, RAAbs from a patient serve as probes to detect specific antigens. Screening proteins obtained from a variety of normal and tumor cells with antibodies from a number of patients regressing tumors allows the identification of molecular species which are essentially unique to human tumor cells. It follows that these antigens elicit the production of RAAbs, the anti-tumor antibodies associated with tumor regression.

The Western immunoblotting procedure consists of the following steps which have been described in Towbin, et al., *Proc. Natl. Acad. Sci (USA)*, 76, 4350 (1979) which reference is incorporated by reference herein. In a typical Western immunoblotting procedure, total cell protein extracts or subcellular fractions are subjected to reducing sodium dodecyl sulfate-polyacrylamide gel electrophoresis (SDS-PAGE). The proteins, which may be RAAs, are transferred by electroelution onto nitrocellulose filters which are subsequently incubated with appropriate dilutions of the test serum or antibody preparation. After the incubation of the filter with antibody, which contain RAAbs, and extensive washing, the filter is incubated with $I^{125}$-labeled Protein A of *Staphylococcus aureus* (which specifically binds to the Fc region of antibody molecules), washed to remove unbound Protein A and exposed to X-ray film for autoradiography. Each radioactive band represents the location of a protein species which formed an immunecomplex with antibodies from the test sera.

The specificities and titers of RAAbs from patients undergoing intralymphatic immunotherapy as described above have been determined using Western immunoblotting by allowing the RAAbs from patient sera to react with immobilized, denatured proteins extracted from human tumor cells including the neoplastic cell vaccines. Analysis of various dilutions of serum samples obtained at different times during the course of intralymphatic immunotherapy has allowed the estimation of titers of antibodies directed against one or more of three specific antigens present in human tumor cells. As also described below, changes in titer as well as specificities of RAAbs have served to monitor the success of the therapy leading to tumor regression or stabilization.

Using techniques essentially as described above, RAAbs from a large number of tumor-regressing patients have detected one or more of three RAAs with apparent molecular weights of 68,000 daltons, 43,000 dalton and 20,000 daltons in various tumor cells including tumor cell vaccines Antibodies in sera prior to immunotherapy failed to detect any of these three RAAs.

Following intralymphatic immunotherapy with tumor cell vaccines, such RAAbs are also found in the ascites fluid from patients exhibiting tumor regression by using the Western immunoblotting technique on extracts of cells containing RAAs. The approximate sizes of the RAAs have been determined based upon the mobility, in reducing SDS-PAGE, of each of the detected RAAs relative to commercially available prestained molecular weight size markers purchased from the Bethesda Research Laboratories, Inc., Bethesda, Md. One such RAA with an assigned molecular weight of 68,000 daltons (68K) migrates within a size of between 65 to 71 thousand daltons. Another RAA consists of either a single protein band of approximately 43,000 daltons (43K) in size within a range of between 41 to 45 thousand daltons, or frequently a doublet consisting of two detectable bands visualized on a Western immunoblot. The third species is an antigen of approximately 20,000 dalton molecular weight (20K) within a range of between 19 to 23 thousand daltons.

Various RAAs have beeen detected in various human tumor tissue and cell extracts using between 200- and 2000-fold dilutions of sera from patients regressing a variety of human malignancies including ovarian carcinoma, thyroid cancer, malignant melanoma, prostate cancer, epidermoid cancer, squamous cell carcinoma and others.

The following Table 1 summarizes results obtained with sera from five patients showing regression of the indicated metastatic cancers following intralymphatic immunotherapy. Sera from the patient indicated above each group of results were used to detect RAAs in extracts of tumor tissues (for example F, O, L and P), established tumor cell lines (A375) or primary short-term cell cultures established from tumor specimens (all other entries). For each RAA species, a "+" indicates detection of a radioactive immune complex band in a standard immunoblot assay using 20 micrograms or less of total cellular proteins and a dilution of 200-fold or more of the sera from the indicated patient.

TABLE 1

| DISTRIBUTION OF RAAs IN TUMOR CELL LINES | | | | |
|---|---|---|---|---|
| Cell line or tumor extract | Ability to Induce Regression | 43K RAA | 68K RAA | 20K RAA |
| PATIENT #1 | | | | |
| extract F (melanoma) | NT | + | + | − |
| M14 | Rg+ | + | − | NT |
| 69-12 | Rg− | − | − | − |
| A375 | NT | + | + | + |
| PATIENT #2 | | | | |
| extract 0 (ovarian carcinoma) | NT | − | + | NT |
| 69-1 | Rg+ | + | + | NT |
| 69-3 | Rg+ | + | + | NT |
| 69-11 | Rg− | − | + | NT |
| Fro81-2 | Rg+ | + | − | NT |
| PATIENT #3 | | | | |
| extract L (squamous cell carcinoma) | NT | − | + | NT |
| 69-2 | Rg+ | + | + | NT |
| 69-13 | Rg+ | − | + | NT |
| Sro82-3 | NT | − | + | NT |
| PATIENT #4 | | | | |
| extract P (prostate carcinoma) | NT | + | + | NT |
| Sro84-1 | Rg+ | + | + | NT |
| PATIENT #5 (thyroid cancer) | | | | |
| Aro81-1 | Rg+ | + | − | NT |
| Dro82-1 | Rg+ | + | − | NT |

ILI status is identified as: Rg+, indicating that the cell lines elicited tumor regression in ILI patients, or Rg− indicating that the cell lines have thusfar failed to elicit tumor regression in ILI patients. NT means not tested.

In all cases in Table 1, the results of immunoblotting analysis carried out with pre-immunotherapy sera indicate the absence of antibodies reacting with any of the respective RAAs for those patients. In several other cases evaluated, with the exception of two patients with malignant melanomas, the results of analysis carried out with pre-immunotherapy serum failed to reveal radioactive bands at about 68K, about 43K or about 20K, suggesting that most cancer patients prior to therapy do not contain antibodies against the RAAs of this invention. The detection of RAAs in the two melanoma patients prior to treatment with intralymphatic immunotherapy may be indicative of the known ability of melanomas to occasionally undergo spontaneous regression.

In additional studies of patients subjected to immunotherapy but in whom no clinical responses were observable (i.e., progression of the malignant condition continued as judged by clinical criteria including radiological analysis or direct physical examination), the results have been analogous to those obtained using sera from patients prior to immunotherapy. Sera evaluated at different times after initiating intralymphatic immunotherapy for many such non-responding patients with several different types of malignancies failed to react with the RAAs in the tumor extracts and in tumor cell lines tested.

The simple method of Western blotting using serum samples from patients and extracts of tumor cells which contain RAAs as demonstrated by experimental results of this invention allows monitoring the quantitative success of an immunotherapy protocol. The monitoring may be accomplished by examining the RAAb titer(s) (defined as the maximal serum dilution able to yield detectable RAAs in a standard Western blot procedure as described below) and the RAAb specificities.

EXAMPLE 2

Monitoring of titers of RAAb's in patients regressing tumors after intralymphatic immunotherapy. Serum samples from patients undergoing immunotherapy are tested as described above using Western immunoblotting of various human tumor cell extracts containing RAAs. Various dilutions of sera samples from each patient are evaluated for the ability to detect one or more of the specific size RAAs.

RAAbs have thus been quantitated in sera obtained at different times after initiating a therapy in a patient with metastatic ovarian cancer. Approximately six weeks after initiation of immunotherapy, one patient's serum had an RAAb titer of ca. 1:2000 against the 43K RAA and this titer reached 1:5000 three months later. Similar demonstrable elevations in titers of RAAbs to one or more RAA have been observed in patients as they start to regress their tumors subsequent to intralymphatic treatment of various other malignancies.

The assay presented here for the quantitation of RAAb titer may also be used in monitoring the effects of other drugs on patients undergoing immunotherapy. This is illustrated by results obtained with a thyroid cancer patient who demonstrated tumor regression after intralymphatic immunotherapy but was subsequently treated with high dose of prednisone for symptoms of shortness of breath. Such steroid therapy is known to suppress the immune system. Within 5 days after initiating high dose prednisone therapy, there was complete elimination of detectable RAAb titer against the 68K RAA as compared to a titer of 1:2000 detected previously in the same patient. Thus, the formation of RAAbs follows a normal course of active immune response to an antigen in that the RAAb titer is suppressed by immunosuppressants such as prednisone.

EXAMPLE 3

Monitoring the specificities of RAAbs in patients undergoing intralymphatic immunotherapy toward RAAs. The techniques according to the present invention are useful in the assessment of response to immunotherapy not only for determining the titer of RAAbs but also for determining the level of the RAAs to which the RAAbs are directed. Different reactivities develop during the course of immunotherapy, as demonstrated by result for one patent with an initial one directed against one band in the 43,000 dalton range followed by appearance of RAAbs reacting with the second rapidly migrating band which was slightly smaller in size than the initial 43,000 dalton RAA and also with the 68,000 dalton RAA. The detection of RAAbs correlates in this patient with the complete regression of pulmonary metastasis from the ovarian adenocarcinoma. Similarly, in a second patient the detection of RAAbs to the 43K and the 68K RAAs coincided with reduction in size of the pulmonary metastasis of thyroid cancer as well as a profound improvement in the patients sense of well-being and physical stamina and appetite.

The specific RAAs of this invention found in human tumor cells are distinguishable from one another and also from other antigens associated with tumors based upon their sizes and immunological properties. Carcinoembryonic antigen (CEA) is much larger than any of the RAAs, as are several of the antigenic determinants identified with murine monoclonal antibodies. Human chorionic gonadotropin (HCG) consists of two subunits both of which are distinguishable from the RAAs described in a reducing SDS-PAGE system (the beta subunit of HCG is 35,000 daltons in size and its alpha subunit is 16,000 daltons in size).

There is a rapidly growing list of tumor-specific antigens identified with murine monoclonal antibodies. The available information distinguishes these antigens from RAAs of this invention on the basis of size or relatedness to normal cellular constituents (*Monoclonal Antibodies and Cancer Therapy*, Reisfeld et al., eds., *supra*). Additional monoclonal antibodies have lead to the detection of a 92K, a 23K, and a 17K antigen in urinary bladder cancer. Ben-Aissa et al., *Br. J. Cancer*, 52, 65–72 (1985).

A monoclonal antibody specific for a 43K surface protein of human leukemia cell line (THP-1) cross-reacts with the intermediate filament of vimentin found in normal cells. Herman et al., *J. Cell Sci.*, 73, 87–103 (1985). A 52K protein is released by human breast cancer cells [Capony et al., *Biochem. Biophys. Res. Commun.*, 108, 8–15 (1982)]and a high molecular weight glycoprotein (220K to 400K) as well as a 90K protein in membrance of human breast cancer [Schlom et al., *Cancer*, 54, 2777–2794 (1984)]. A sarcomaspecific 70K antigen appears to be different from the 68K RAA of this invention in that the 70K antigen was not detectable in carcinoma cell lines (Feit et al., *Cancer Res.*, 44, 5752–5756, (1984).

Twenty-Six patients who underwent tumor regression following intralymphatic tumor vaccine immunotherapy for a variety of different cancers were investigated and the quantitation of RAAbs, determined as above, correlated directly with tumor regression in these patients. A variety of control extracts from normal human tissues have been screened with post-immunotherapy sera from these patients and no reactivities have been identified with antigenic species comparable to the RAAs described in this invention. No non-regressor patients out of 6 evaluated had detectable RAAbs. In addition, over 20 serum samples obtained randomly from patients with different human malignancies were screened in the Western immunoblotting technique using extracts of three tumor cell lines (squamous cell carcinoma, malignant melamona and ovarian carcinoma) and no reactivities were detected with specific bands in the regions of 20,000 molecular weight, 43,000 molecular weight and 68,000 molecular weight. This correlation of the development of regression-associated antibodies with tumor regression has been made in the 26 patients in whom significant tumor regression was observed after intralymphatic immunotherapy.

EXAMPLE 4

Identification of RAAbs in a patient with metastatic ovarian adenocarcimona and characterization of their RAA-specificities. The patient was a 64 year-old white female who presented with metastatic ovarian adenocarcinoma and involvement of inguinal lymph nodes was examined. A one gram surgical biopsy specimen of the inguinal lymph node was minced using sterile scissors, passed through a gauze mesh and incubated for 1 hour at 37° with collagenase followed by an incubation with trypsin for an additional 30 min. The tumor cell suspension was rinsed in cell culture medium and used to establish a permanent ovarian carcinoma cell line identified as Ing 69-1. This cell line was subsequently used in intralymphatic immunotherapy of this patient from whom the tumor biopsy was obtained. Extracts of this cell line, as well as of A375 cells (available from the American Type Tissue Culture Collection, Rockville, Md., as ATCC No. CRL 1619) and this patient's tumor biopsies were processed for analysis as follows.

Neoplastic cells growing in cell culture or tumor cell suspensions were obtained by mincing fresh tumor biopsy material in an isotonic buffer such as phosphate-buffered saline (PBS) are rinsed in PBS and were subsequently extracted using a mixture ionic and non-ionic detergents according to the procedure of Sen et al., *Proc. Natl. Acad. Sci. (USA)*, 80, 1246–1250 (1983), or solely in a gentle nonionic detergent buffer which preferentially extracts proteins from cell membranes (10 mM Tris-HCl (pH 7.5), 1 mM EDTA, 2.5 mM EGTA, 10 mM $NaMoO_4$, 12 mM monothioglycerol, 10% glycerol, 40 μg/ml leupeptin and 0.2% Triton X-100). Insoluble materials were removed by centrifugation at 10,000×g and the supernatent solution was retained. Aliquots of the supernatent containing 10 to 20 micrograms of cell protein were subjected to reducing SDS-PAGE according to the procedure of Laemmli, Nature, 227, 680–685 (1970) and subsequently electroeluted onto nitrocellulose filters. The filters were blocked in a buffer containing a suitable protein such as bovine serum albumin, ovalbumin or milk proteins to cover the filter completely with protein and thus block nonspecific binding of antibodies from the test serum sample.

Small aliquots of serum were added to give final dilutions between 1 to 200 and 1 to 2000 in the blocking buffer along with the nitrocellulose filter containing the fractionated proteins and specific immune complexes were allowed to form. The specific immune complex formation involving antibody binding to antigens was then detected by treatment of the washed filter by Protein A which only reacts with the Fc region of antibodies. Protein A was radioiodinated with $I^{125}$. The filter was again washed and subsequently was dried and was exposed to X-ray film. The X-ray film was then developed to reveal after autoradiography the specific bands where antigen and antibody complex had formed.

Cell line A375 is a malignant melanoma cell line described by Todaro and colleagues. Giard et al., *J. Nat. Cancer Inst.*, 51, 1417–1423 (1973). In a typical procedure for the isolation of RAAs, A375 cells growing in roller bottles may be washed and subsequently exposed to extraction buffers containing nonionic and ionic detergents as described above which detergents are capable of soublizing proteins on cell membranes or total cellular proteins. After high speed centrifugation (10,000×g, 4° C.) the soluble supernatant is taken for further purification using conventional chromotography steps as well as affinity chromatography (e.g., using resins containing immobilized antibodies specific for regression-associated antigens or lectins with high affinity for these antigens).

Approximately $10^8$ A375 cells growing in roller bottles were rinsed twice with PBS and then were extracted with a small volume (50 ml) of 0.2% Triton X-100 buffer for 5 min. at room temperature. The solution was removed and debris was pelleted by centrifugation (10,000×g, 4° C.). The supernatant containing RAAs was passed over an antibody affinity column prepared by coupling 10 mg of immunoglobulins purified on a Zetachrom TM membrane filter according to supplier's instructions (AMF Lab Products, Meriden, Conn.) from the sera of Patient #2 of Table 1 to an Affi-gel 10 TM resin according to the supplier's instructions (Bio-Rad, Richmond, Calif.). The column was washed with distilled water and RAAs were eluted using 1 M NaCl, 0.1% NP40, 0.5% sodium deoxycholate, 0.1% sodium dodecyl sulfate, 25 mM Tris-HCl, pH 7.5, 1% aprotinin. The eluant was dialyzed against 0.01 M ammonium bicarbonate, frozen and lyophilized.

The lyophilized powder was resuspended in 0.5% trifluoracetic acid and 4 mg total protein was loaded onto a standard C-8 column for high performance liquid chromatography (Beckman Instruments) using a 0 to 100% acetonitrile gradient. Elution was performed using a 0 to 100% acetonitrile gradient going from peak 1 (pass through) to peak 10. Samples of each peak were lyophilized and analyzed by immunoblotting using post-ILI serum (1:1000 dilution) from Patient #2 of Table 1. The Coomassie blue-stained SDS-PAGE revealed that greater than 40% of the detectable protein in peak 6 was in species having 43 K and 63K sizes.

The progress of purification is followed using the Western immunoblotting technique to verify the location of specific 68K and 43K regression-associated antigens using this patient's sera. The degree of purity of products is assessed by determination of protein concentration as well as comparison of total proteins in specific fractions containing regression-associated antigens with the composition of the starting material. This is assessed by staining the SDS-PAGE with Coomasie brilliant blue protein stain or with silver staining to provide a more sensitive indication of total proteins. This general scheme has been used to successfully purify the 43K and 68K antigens from the A375 cell line and has proven effective also for comparable purification from human ovarian and squamous carcinoma cell lines. The general scheme is also expected to permit purification of the 20K antigen from A375 cells. Affinity purification with this patient's antibodies bound to Affi-gel 10 TM has been part of the purification procedure and the last step utilizes high pressure liquid chromatography under standard conditions.

EXAMPLE 5

Antisera may be specifically produced by immunizing rabbits with injections of purified RAAs according to the present invention as follows. A first inoculation may contain an RAA with Freund's complete adjuvant. Succeeding inoculations may contain the RAA and Freund's incomplete adjuvant. The animals are bled to obtain sera. Polyclonal antibodies may be isolated from the sera by conventional techniques known in the art. Alternately, affinity columns containing purified RAAs bound to Affi-gel 10 TM may be prepared using supplier's instructions (Bio-Rad). Highly specific polyclonal antibodies may be prepared using this affinity column by conventional procedures.

EXAMPLE 6

Monoclonal antibodies according to the present invention may be produced according to the procedure of Kohler et al., *Nature*, 256; 495 (1975) with the substitution of a purified solution of RAA according to Example 4 for an antigen employed therein. Schlom et al. is incorporated by reference herein.

Basically, monoclonal antibodies are produced by injecting mice with immunizing doses of RAAs, as described in Example 5. Spleens are removed from the immunized animals, and spleen cells are fused to myeloma cells using a fusogen, such as polyethylene glycol. Hybridoma cells producing monoclonals are selected for in HAT medium. Monoclonal antibodies specific for RAAs may be isolated by affinity chromatography from media in which such hybridomas have been cultured.

EXAMPLE 7

Drugs may be targeted to a tumor according to the present invention. An anti-cancer drug may be bound to a monoclonal antibody against an RAA (mRAAb) of the sort described in Example 6. Such antibody-mediated drug delivery systems are reviewed in Rodwell et al., *Biotechnology*, 3, 889-894 (1985) which is incorporated by reference herein.

By introducing an mRAAb linked to an anticancner drug into a bodily fluid (blood, lymph or any other appropriate fluid such as cerebrospinal, etc.) of a patient, such a drug may be selectively bound to tumor cells expressing an RAA for which the mRAAb is specific. It is anticipated that such binding of a tumor cell with an anticancer drug will adversely affect its survival.

Although the present invention is described in terms of a preferred embodiment, it is understood that modifications and improvements will occur to those skilled in the art. For example, other conventional immunological techniques such radioimmunoassay, immunoprecipitation and ELISA may be suitable for detection of regression-associated antigens.

Accordingly, it is intended that the appended claims include all such equivalent variations which come within the scope of the invention as claimed.

We claim:

1. A method for detecting the presence of regression-associated antibodies comprising the steps of:
   obtaining a first sample of serum from a patient diagnosed as not being in a state of regression and obtaining a second sample from the patient after diagnosis as being in a state of regression;
   separately exposing a component of a neoplastic cell to the first and second samples;
   detecting the absence of immune complex formation between the component of a neoplastic cell and antibodies in the first serum sample; and
   detecting the presence of an immune complex between an antibody in the second sample and the component of a neoplastic cell and thereby detecting a regression-associated antibody in the second sample.

2. A method for monitoring the response of a patient to immunotherapy for symptoms associated with a neoplasm comprising the steps of:
   establishing a first level of regression-associated antibodies indicative of a state of regression;
   determining a second level of regression-associated antibodies in a patient undergoing immunotherapy; and
   comparing the first level with the second level to determine whether the first level is indicative of a state of regression.

3. A method for identifying regression associated antigens comprising the steps of:
   exposing a component of a neoplastic cell to regression-associated antibodies; and
   determining the presence of an immune complex between at least one of the regression-associated antibodies and the component.

4. A method for purification of regression-associated antigens comprising the steps of:
   obtaining a first sample of serum from a patient diagnosed as not being in a state of regression and obtaining a second sample from a patient after diagnosis as being in a state of regression;
   exposing a component of a neoplastic cell to each of the samples;
   detecting the absence of immune complex formation between the component of the neoplastic cell and antibodies in the first serum sample;
   detecting the presence of an immune complex between an antibody and the component of the neoplastic cell;
   disrupting antigenic materials on the neoplastic cell into solution components;
   chromatographically separating components of the solution into fractions; and
   identifying fractions containing regression associated antigens by the presence of immune complex formation of components of a fraction with antibodies to regression-associated antigens.

5. A purified and isolated antigen selected form the group consisting of human regression associated antigens having a molecular weight as determined by reducing SDS polyacrylamide gel electrophoresis within the range of:
   about 19,000 to about 23,000 daltons;
   about 41,000 to about 45,000 daltons; and
   about 65,000 to about 71,000;
   said regression-associated antigens being characterized by formation of an immune complex with an antibody present in a serum sample from a pateitn after the patient is diagnosed as being in a state of regression and being further characterized by the absence of an immune complex with an anitbody present in a serum sample from a patient before diagnosis as being in a state of regression.

6. Immunotherapy comprising the step of injecting an immunogenic amount of an antigen as recited in claim 5 into a patient to provoke an immune response.

7. A method for monitoring the metastasis of a tumor in a patient comprising the steps of:
   determining the level of a regression-associated antigen in a sample of a bodily fluid;
   comparing the level of the regression-associated antigen in the sample with a criterion for metastasis and thereby monitoring metatasis of a tumor in the patient.

8. A monoclonal or monospecific polyclonal antibody exhibiting a specific immunoreactivity with an antigen selected from the group consisting of human regression associated antigens having a molecular weight as determined by reducing SDS polyacrylamide gel electrophoresis within the range of:

about 19,000 to about 23,000 daltons;
about 41,000 to about 45,000 daltons; and
about 65,000 to about 71,000;
said regression-associated antigens being characterized by formation of an immune complex with an antibody present in a serum sample from a patient after the patient is diagnosed as being in a state of regression and being further characterized by the absence of an immune complex with an antibody prepset in a serum sample from the patient before diagnosis as being in a state of regression.

9. A method for purifying an antibody according to claim 8 comprising the steps of:
contacting a substrate-bound antigen selected from the group consisting of human regression associated antigens having a molecular weight as determined by reducing SDS polyacrylamide gel electrophoresis within the range of:
about 19,000 to about 23,000 daltons;
about 41,000 to about 45,000 daltons; and
about 65,000 to about 71,000;
said regression-associated antigens being characterized by formation of an immune complex with an antibody present in a serum sample from a patient after the patient is diagnosed as being in a state of regression and being further qharacterized by the absence of an immune complex with an antibody present in a serum sample from the patient before diagnosis as being in a state of regression, with a solution containing an antibody exhibiting specific immunoreactivity with said antigen; and
eluting the antibody from the antigen.

10. A drug delivery method for tumor therapy comprising the steps of:
binding a drug to a monoclonal or monospecific polyclonal antibody exhibiting a specific immunoreactivity with an antigen selected from the group consisting of human regression associated antigens having a molecualr weight as determined by reducing SDS polyacrylamide gell electrophoresis within the range of:
about 19,000 to about 23,000 daltons;
about 41,000 to about 45,000 daltons; and
about 65,000 to about 71,000;
said regression-associated antigens being characterized by formation of an immune complex with an antibody present in a serum sample from a patient after the patient is diagnosed as being in a state of regression and being further characterized by the absence of an immune complex with an antibody present in a serum sample from the patient before diagnosis as being in a state of regression; and
introducing the antibody-bound drug into a bodily fluid of a patient.

11. A method for immunotherapy of tumors comprising the steps of:
obtaining a first sample of serum from a patient diagnosed as not being in a state of regression and obtaining a second sample from a patient after diagnosis as being in a state of regression;
separately exposing a component of a neoplastic cell to the first and second samples;
determining the absence of immune complex formation between the component of the neoplastic cell and anti-bodies in the first serum sample;
determining the presence of immune complex formation between an antibody and the component of the neoplastic cell; and
introducing the neoplastic cell, or membrane fractions thereof or regression associated antigens isolated therefrom into lymphatic or hematic fluid within a patient.

* * * * *

UNITED STATES PATENT AND TRADEMARK OFFICE
CERTIFICATE OF CORRECTION

PATENT NO. : 4,748,112

DATED : May 31, 1988

INVENTOR(S) : George C. Fareed and Arup Sen

It is certified that error appears in the above-identified patent and that said Letters Patent is hereby corrected as shown below:

At column 9, line 14, delete "available from" and substitute --deposited on February 12, 1987 with-- therefor.

At column 9, line 16, delete "CRL 1619" and substitute --ATCC CRL 9321-- therefor.

Signed and Sealed this

Seventeenth Day of March, 1992

Attest:

HARRY F. MANBECK, JR.

Attesting Officer     Commissioner of Patents and Trademarks